United States Patent
Masuda et al.

(10) Patent No.: US 9,289,371 B2
(45) Date of Patent: Mar. 22, 2016

(54) EMULSION AND COSMETIC COMPOSITION

(71) Applicant: Nissin Chemical Industry Co., Ltd., Echizen-shi, Fukui-ken (JP)

(72) Inventors: Yukihiro Masuda, Echizen (JP); Kentaro Watanabe, Echizen (JP); Akira Yamamoto, Echizen (JP)

(73) Assignee: NISSAN CHEMICAL INDUSTRY CO., LTD., Echizen-Shi (JP)

( * ) Notice: Subject to any disclaimer, the term of this patent is extended or adjusted under 35 U.S.C. 154(b) by 0 days.

(21) Appl. No.: 14/467,524

(22) Filed: Aug. 25, 2014

(65) Prior Publication Data

US 2015/0056152 A1 Feb. 26, 2015

(30) Foreign Application Priority Data

Aug. 26, 2013 (JP) ................................. 2013-174421

(51) Int. Cl.
| | | |
|---|---|---|
| C08F 2/22 | (2006.01) | |
| A61K 8/891 | (2006.01) | |
| A61K 8/46 | (2006.01) | |
| A61K 8/06 | (2006.01) | |
| A61Q 1/10 | (2006.01) | |
| C08F 2/24 | (2006.01) | |
| C08F 283/12 | (2006.01) | |
| A61Q 1/02 | (2006.01) | |
| A61Q 17/04 | (2006.01) | |
| A61K 8/81 | (2006.01) | |
| C08F 4/40 | (2006.01) | |

(52) U.S. Cl.
CPC . *A61K 8/891* (2013.01); *A61K 8/06* (2013.01); *A61K 8/466* (2013.01); *A61K 8/8129* (2013.01); *A61Q 1/02* (2013.01); *A61Q 1/10* (2013.01); *A61Q 17/04* (2013.01); *C08F 2/24* (2013.01); *C08F 4/40* (2013.01); *C08F 283/122* (2013.01)

(58) Field of Classification Search
CPC ........ A61K 8/891; A61K 8/8152; C08F 2/24; C08F 220/06; C08F 220/00
See application file for complete search history.

(56) References Cited

U.S. PATENT DOCUMENTS 3,898,300 A * 8/1975 Hilliard ............... C08F 283/124
525/104

FOREIGN PATENT DOCUMENTS

| EP | 1 736 138 A1 | 12/2006 |
|---|---|---|
| JP | 7-196449 A | 8/1995 |
| JP | 9-143029 A | 6/1997 |
| JP | 9-175940 A | 7/1997 |
| JP | 11-43417 A | 2/1999 |
| JP | 2011-213708 A | 10/2011 |
| WO | WO 2011/087767 A1 | 7/2011 |

OTHER PUBLICATIONS

Extended European Search Report issued Jan. 26, 2015, in European Patent Application No. 14181470.7.

* cited by examiner

*Primary Examiner* — Kuo-Liang Peng
(74) *Attorney, Agent, or Firm* — Birch, Stewart, Kolasch & Birch, LLP

(57) ABSTRACT

An emulsion is obtained from emulsion polymerization of a mixture of (a) 1-50 wt % of a triorganosiloxysilicic acid and (b) 50-99 wt % of an ethylenically unsaturated monomer in the presence of (c) an emulsion stabilizer which is an anionic surfactant, nonionic surfactant or polyvinyl alcohol. The emulsion is used to formulate a cosmetic composition capable of forming, on drying, a film which has water resistance, oil resistance and toughness and is thus effective for preventing makeup deterioration. The cosmetic composition containing the emulsion is useful as eyeliner, mascara, eyebrow color, liquid foundation or milky lotion.

10 Claims, No Drawings

EMULSION AND COSMETIC COMPOSITION

CROSS-REFERENCE TO RELATED APPLICATION

This non-provisional application claims priority under 35 U.S.C. §119(a) on Patent Application No. 2013-174421 filed in Japan on Aug. 26, 2013, the entire contents of which are hereby incorporated by reference.

TECHNICAL FIELD

This invention relates to an emulsion and a cosmetic composition comprising the emulsion.

BACKGROUND ART

Makeup cosmetic compositions are generally composed of a powder component such as talc, mica, titania or coloring pigment, an oil component such as oils, fats, hydrocarbons, higher fatty acids, higher alcohols, triglycerides, ester oil or silicone oil, surfactants, polyhydric alcohols, polymers, an aqueous component, and the like. There are available makeup cosmetics of diverse types including solid foundations, liquid foundations, eye shadows, cheek colors, lip colors, eyeliners, mascara, sunscreen lotions, and the like, and in various forms including solid, non-aqueous, W/O emulsion, O/W emulsion, aqueous and the like.

From the aspects of feeling on use and daily UV protection, makeup cosmetic compositions are desired to have lasting quality. Particularly in summer or hot humid conditions and sports, they are desired to have water resistance, oil resistance and persistence. Coatings of makeup cosmetic compositions tend to undergo wrinkling and blotting due to sweat, sebum or the like, deteriorations such as peeling by contact, and cosmetic transfer such as staining to cups and cigarettes. One countermeasure taken in the art is by formulating synthetic resin emulsions or silicone resins having a film-forming ability in cosmetic compositions.

In general, coatings of synthetic resin emulsions are less water resistant in that they are susceptible to breakage or separation when wetted with water. Thus they are not satisfactory in lasting quality of cosmetics. For example, acrylic resin emulsions are often used in cosmetic compositions, but there is a likelihood of cosmetic spoiling due to short adhesion caused by the toughness of film. There is a demand for an emulsion for cosmetic use having higher water resistance and lasting quality.

One class of silicone resin commonly used includes triorganosiloxysilicic acids such as trimethylsiloxysilicic acid. For example, JP-A H09-143029 and JP-A H09-175940 disclose that a solution of trimethylsiloxysilicic acid in cyclic silicone is formulated in sunscreen lotions and cosmetic bases. It is known that formulating a silicone resin solution is effective for improving the feeling on use and lasting quality of cosmetics. However, when a silicone resin solution is applied in a model experiment and an actual use, the effect obtained on the actual use is not comparable to the effect obtained in the model experiment. This is because the cyclic silicone does not volatilize off, but remains on the skin and eventually prevents the silicone resin from exerting its effect.

JP-A H07-196449 discloses an eye makeup cosmetic composition comprising trimethylsiloxysilicic acid, a specific acrylic-silicone based graft copolymer, and a low-boiling silicone oil and/or low-boiling isoparaffin, which forms a uniform film with improved water resistance, sebum resistance, and lasting quality. Since the film is still insufficient in uniformity, water resistance, and sebum resistance, improvements in these properties are desired.

When trimethylsiloxysilicic acid is formulated in cosmetic compositions, the formulating technique involving dissolution in an organic solvent and subsequent emulsification is generally used in the prior art as alluded to in the cited patent documents. In the resulting mixture, trimethylsiloxysilicic acid is not uniformly admixed with the silicone component. For example, the method of JP-A H07-196449 can form a sea-island structure on the copolymer level, but there is still left a room for improvement in uniformity. This causes a film to become very hard, giving uncomfortable or stiff feel on the skin or heavy touch upon application. As the amount of trimethylsiloxysilicic acid blended is increased in order to prevent cosmetic spoiling, emulsification is retarded, making it difficult to obtain satisfactory storage stability. There exists a demand for a technique of uniformly formulating trimethylsiloxysilicic acid in cosmetic compositions.

CITATION LIST

Patent Document 1: JP-A H09-143029
Patent Document 2: JP-A H09-175940
Patent Document 3: JP-A H07-196449

DISCLOSURE OF INVENTION

An object of the invention is to provide an emulsion which has comfortable feel on touch and long-term storage stability, and on drying, forms a film that possesses water resistance, oil resistance and toughness enough to prevent makeup spoiling, and a cosmetic composition comprising the emulsion.

The inventors have found that an emulsion obtained from polymerization of a mixture of a triorganosiloxysilicic acid and an ethylenically unsaturated group-containing monomer ensures uniform distribution of silicone component on the molecular level, is capable of forming a film having water resistance, oil resistance and toughness and thus effective for preventing makeup deterioration when used as cosmetics.

In one aspect, the invention provides an emulsion obtained from emulsion polymerization of a mixture of (a) 1 to 50% by weight of a triorganosiloxysilicic acid and (b) 50 to 99% by weight of an ethylenically unsaturated group-containing monomer, the total of components (a) and (b) being 100% by weight, in the presence of (c) at least one emulsion stabilizer selected from the group consisting of an anionic surfactant, nonionic surfactant, and polyvinyl alcohol.

Typically, the triorganosiloxysilicic acid (a) comprises $SiO_2$ units and $R_3SiO_{0.5}$ units (wherein R is an alkyl group of 1 to 6 carbon atoms) in a molar ratio of 0.5 to 2.0, and the total amount of $SiO_2$ units and $R_3SiO_{0.5}$ units accounts for at least 90 mol % of the triorganosiloxysilicic acid (a). Especially, the triorganosiloxysilicic acid (a) is trimethylsiloxysilicic acid in which R is methyl in $R_3SiO_{0.5}$ units.

The ethylenically unsaturated group-containing monomer (b) is preferably selected from among ethylene, propylene, chlorine-containing ethylenically unsaturated monomers, aromatic vinyl monomers, vinyl carboxylate monomers, conjugated diene monomers, ethylenically unsaturated monocarboxylic acid esters, ethylenically unsaturated dicarboxylic acid esters, ethylenically unsaturated monocarboxylic acids, ethylenically unsaturated dicarboxylic acids, alcoholic hydroxyl-containing ethylenically unsaturated monomers, epoxy-containing ethylenically unsaturated monomers, alkoxy-containing ethylenically unsaturated monomers, nitrile-containing ethylenically unsaturated monomers, amide-containing ethylenically unsaturated monomers, amino-containing ethylenically unsaturated monomers, monomers having at least two ethylenically unsaturated groups, and mixtures thereof.

More preferably, the ethylenically unsaturated group-containing monomer (b) is acrylic acid, methacrylic acid, an alkyl acrylate, an alkyl methacrylate, or a mixture comprising two or more thereof.

The stabilizer (c) is preferably an acylamino acid salt, acyltaurine salt, aliphatic soap, alkyl phosphate, or a mixture of two or more thereof.

Typically the emulsion is used in cosmetics.

In another aspect, the invention provides a method for preparing an emulsion comprising the steps of:

dissolving (a) 1 to 50% by weight of a triorganosiloxysilicic acid in (b) 50 to 99% by weight of at least one ethylenically unsaturated group-containing monomer to form a mixture, the total of components (a) and (b) being 100% by weight, adding 0.1 to 20 parts by weight of (c) at least one emulsion stabilizer selected from the group consisting of an anionic surfactant, nonionic, surfactant, and polyvinyl alcohol to 100 parts by weight of the mixture, and effecting emulsion polymerization.

In a further aspect, the invention provides a makeup cosmetic composition comprising 0.1 to 30% by weight (calculated as solids and based on the composition) of the emulsion defined above, which composition is a skin care product, mascara, eyeliner, eyebrow color or foundation.

Advantageous Effects of Invention

The emulsion of the invention is used to formulate a cosmetic composition capable of forming, on drying, a film which has water resistance, oil resistance and toughness and is thus effective for preventing makeup deterioration, and can be readily cleansed off with weakly alkaline agents such as soaps. The cosmetic composition containing the emulsion is useful as eyeliner, mascara, eyebrow color, liquid foundation, milky lotion (e.g., sunscreen) or the like.

DESCRIPTION OF PREFERRED EMBODIMENT

According to the invention, an emulsion is obtained from emulsion polymerization of a mixture of (a) a triorganosiloxysilicic acid and (b) an ethylenically unsaturated group-containing monomer in the presence of (c) an emulsion stabilizer.

The triorganosiloxysilicic acid (a) is preferably selected from trialkylsiloxysilicic acids having an alkyl group of 1 to 6 carbon atoms, for example, trimethylsiloxysilicic acid, triethylsiloxysilicic acid, tripropylsiloxysilicic acid, and tributylsiloxysilicic acid. Inter alia, trimethylsiloxysilicic acid is most preferred. Trialkylsiloxysilicic acid is a crosslinked structure compound having a siloxane structure as main skeleton, that is, a silicone resin composed mainly of $SiO_2$ units and $(R)_3SiO_m$ units (wherein R is $C_1$-$C_6$ alkyl), especially $(CH_3)_3SiO_{0.5}$ units. The triorganosiloxysilicic acid may further comprises $(R)_2SiO_{1.0}$ units and/or $(R)_1SiO_{1.5}$ units. However, it is preferred that the total amount of $SiO_2$ units and $(R)_2SiO_{0.5}$ units accounts for at least 90 mol % (i.e., 90 to 100 mol %).

The weight average molecular weight of the triorganosiloxysilicic acid is preferably 100 to 50,000, more preferably 500 to 10,000, most preferably 1,000 to 8,000, as measured by gas permeation chromatography (GPC) versus polystyrene standards. If the weight average molecular weight of the triorganosiloxysilicic acid is more than 50,000, the solubility of the triorganosiloxysilicic acid to a solvent may be lowered.

The triorganosiloxysilicic acid is used in the form of a powder or a solution in which the triorganosiloxysilicic acid is dissolved in a solvent. In this case, cyclic siloxanes such as decamethylcyclopentasiloxane and cyclopentasiloxane, dimethylsilicone oils, and isododecane. The content of the triorganosiloxysilicic acid in the solution is preferably 30 to 80% by weight, more preferably 40 to 70% by weight.

The triorganosiloxysilicic acid or silicone resin is not particularly limited as long as it is commonly used in cosmetics. Useful silicone resins are commercially available under the trade name of KF-73123, KF-7312K, X-21-5249, X-21-5250 and KF-9021 from Shin-Etsu Chemical Co., Ltd., TMS803 from Wacker Silicone, SR1000 and TSF4600 from GE-Toshiba Silicone Co., Ltd., DC593 and BY11-018 from Dow Corning-Toray Silicone Co., Ltd. The silicone resin may be used either as solution in various solvents or in powder form. The silicone resin in powder form having an average particle size of 1 to 30 μm is preferred because purification concomitant with drying for atomization is expectable. Notably, the average particle size is a weight average value $D_{50}$ as measured for particle size distribution by the laser light diffraction method.

Examples of the ethylenically unsaturated group-containing monomer (b) include ethylene, propylene, chlorinated monomers such as vinyl chloride and vinylidene chloride; vinyl carboxylate monomers such as vinyl acetate and vinyl propionate; aromatic vinyl monomers such as styrene and α-methylstyrene; conjugated diene monomers such as 1,3-butadiene and 2-methyl-1,3-butadiene; ethylenically unsaturated monocarboxylic acid esters such as methyl acrylate, ethyl acrylate, butyl acrylate, 2-ethylhexyl acrylate, and methyl methacrylate; ethylenically unsaturated dicarboxylic acid esters such as dimethyl itaconate, diethyl maleate, monobutyl maleate, monoethyl fumarate, and dibutyl fumarate; ethylenically unsaturated monocarboxylic acids such as acrylic acid, methacrylic acid and crotonic acid; ethylenically unsaturated dicarboxylic acids such as itaconic acid, maleic acid, and fumaric acid; epoxy-containing monomers such as glycidyl methacrylate; alcoholic hydroxyl-containing monomers such as 2-hydroxyethyl methacrylate; alkoxy-containing monomers such as methoxyethyl acrylate; nitrile-containing monomers such as acrylonitrile; amide-containing monomers such as acrylamide; amino-containing monomers such as dimethylaminoethyl methacrylate; and monomers containing at least two ethylenically unsaturated groups in a molecule such as divinylbenzene and allyl methacrylate, which may be used alone or in admixture of two or more.

Of these, the preferred ethylenically unsaturated group-containing monomers include (meth)acrylates such as methyl acrylate, ethyl acrylate, n-butyl acrylate, lauryl acrylate, methyl methacrylate, ethyl methacrylate, and n-butyl methacrylate; styrene monomers such as styrene and chlorostyrene; N-substituted (meth)acrylamides such as t-butyl acrylamide; acrylonitrile and methacrylonitrile. More preferably, ethylenically unsaturated group-containing monomers selected from acrylic acid, methacrylic acid, alkyl acrylates, and alkyl methacrylates are used alone or in admixture of two or more.

The triorganosiloxysilicic acid (a) and the ethylenically unsaturated group-containing monomer (b) are mixed in such amounts that the mixture may consist of 1 to 50% by weight of the triorganosiloxysilicic acid (a) and 50 to 99% by weight of the monomer (b), preferably 1 to 40% by weight of the triorganosiloxysilicic acid (a) and 60 to 99% by weight of the monomer (b). If the amount of the triorganosiloxysilicic acid (a) added is less than 1% by weight, a film after drying fails to exert its addition effect. If the amount of the triorganosiloxysilicic acid (a) added exceeds 50% by weight, a film after drying becomes white and opaque and thus unsuitable as cosmetics. It is noted that the total of components (a) and (b) is 100% by weight.

The emulsion stabilizer (c) is selected from among an anionic surfactant, nonionic surfactant, polyvinyl alcohol (PVA), and mixtures of two or more. Any emulsion stabilizers are acceptable as long as they are commonly used in cosmetics. Suitable anionic surfactants include fatty acid soaps such as sodium stearate and triethanolamine palmitate; alkyl ether carboxylic acids and salts thereof, carboxylic acid salts such as condensates of amino acids and fatty acids, alkylsulfonic acids, alkenesulfonic acid salts, sulfonic acid salts of fatty acid esters, sulfonic acid salts of fatty acid amides, sulfonic acid salts such as alkylsulfonic acid salts and formalin condensates thereof, alkylsulfuric acid ester salts, secondary higher alcohol sulfuric acid ester salts, alkyl and allyl ether sulfuric acid ester salts, fatty acid ester sulfuric acid ester salts, sulfuric acid ester salts of fatty acid alkylol amides, polyoxyethylene alkylsulfuric acid ester salts, sulfuric acid ester salts such as Turkey red oil, alkyl phosphoric acid salts, ether phosphoric acid salts, alkyl allyl ether phosphoric acid salts, amide phosphoric acid salts, and N-acylamino acids. Suitable nonionic surfactants include glycerol fatty acid esters and alkylene glycol adducts thereof, polyglycerol fatty acid esters and alkylene glycol adducts thereof, propylene glycol fatty acid esters and alkylene glycol adducts thereof, sorbitan fatty acid esters and alkylene glycol adducts thereof, sorbitol fatty acid esters and alkylene glycol adducts thereof, polyalkylene glycol fatty acid esters, polyoxyalkylene alkyl ethers, glycerol alkyl ethers, polyoxyethylene alkyl phenyl ethers, polyoxyethylene-hardened castor oil, and alkylene glycol adducts of lanolin. Suitable polyvinyl alcohols include PVA's having an average degree of polymerization of 500 to 4,000 and PVA's having a degree of saponification of 70 to 98 mol %, preferably 80 to 95 mol %.

The preferred emulsion stabilizers include acylamino acid salts, acyltaurine salts, fatty acid soaps, alkyl phosphates, and polyvinyl alcohol. Inter alia, sodium lauroylmethyltaurine, sodium myristoylmethyltaurine, and polyvinyl alcohol are most preferred.

The emulsion stabilizer (c) is preferably used in an amount of 0.1 to 20 parts by weight, more preferably 5 to 15 parts by weight per 100 parts by weight of the mixture of the triorganosiloxysilicic acid (a) and the ethylenically unsaturated group-containing monomer (b). Outside the range, a less amount of the emulsion stabilizer may fail emulsification or lead to extreme instability whereas a larger amount may interfere with the reaction.

For polymerization of the mixture containing the triorganosiloxysilicic acid (a), the ethylenically unsaturated group-containing monomer (b), and the emulsion stabilizer (c), any well-known emulsion polymerization techniques may be used. The triorganosiloxysilicic acid (a), the monomer (b), the emulsion stabilizer (c), and an optional polymerization aid such as a polymerization initiator, chain transfer agent (e.g., mercaptans), pH modifier (e.g., sodium carbonate), or defoamer may be added all together at the start, or continuously added. Alternatively, one or more components may be added continuously or in divided portions during polymerization.

Suitable polymerization initiators include persulfates such as ammonium persulfate and potassium persulfate, azo compounds such as 2,2'-diamidino-2,2'-azopropane dihydrochloride and azobisisobutyronitrile, and peroxides such as cumene hydroperoxide, benzoyl peroxide, and hydrogen peroxide. Also included are well-known redox initiators such as potassium persulfate and sodium hydrogen sulfite, and hydrogen peroxide and L-ascorbic acid (vitamin C). The polymerization initiator is preferably used in an amount of 0.01 to 10 parts by weight, more preferably 0.1 to 2 parts by weight per 100 parts by weight of the mixture of the triorganosiloxysilicic acid (a) and the ethylenically unsaturated group-containing monomer (b).

For emulsion polymerization, the reaction temperature is typically 50 to 95° C., preferably 60 to 85° C. and the reaction time is typically 1 to 40 hours, preferably 4 to 10 hours. Polymerization is preferably conducted in an inert gas atmosphere such as nitrogen gas.

The resulting reaction product or emulsion should preferably have a solid content of 10 to 60% by weight, more preferably 20 to 50% by weight. Outside the range, an emulsion with a lower solid content may fail to exert the desired effect whereas an emulsion with a higher solid content may be unstable. The solid content may be adjusted using water or an organic solvent.

The emulsion preferably has a viscosity of 10 to 5,000 mPa·s at 25° C., more preferably 50 to 1,000 mPa·s at 25° C. The viscosity is measured by a Brookfield viscometer under conditions: No. 1 rotor, 6 rpm and 1 minute.

Preferably, the emulsion has an average particle size of up to 1 μm, more preferably 100 to 600 nm, as measured by a particle size distribution analyzer of laser diffraction scattering method; pH 6 to 8; and a glass transition temperature (Tg) of about −50° C. to 30° C., more preferably about −20° C. to 0° C.

On drying, the emulsion thus obtained forms a film having water repellency (water resistance), oil resistance, and toughness. The emulsion is thus expected to find application as cosmetics such as skin care products, mascara, eyeliner, and foundations.

In another aspect, the invention provides a cosmetic composition comprising the emulsion. The emulsion is preferably formulated in an amount of 0.1 to 40% by weight, preferably 1 to 30% by weight calculated as solids and based on the cosmetic composition. Less than 0.1% by weight of the emulsion (as solids) may fail to obtain the desired effect whereas more than 40% by weight of the emulsion may be unfavorable as cosmetics.

Besides the emulsion, other ingredients such as oil, solvent, and powder may be formulated in the cosmetic composition. Suitable oils include hydrocarbons, silicone oils, triglyceride, ester oils, oils and fats, waxes, higher fatty acids of 12 to 20 carbon atoms, and higher alcohols of 8 to 20 carbon atoms. Inter alia, low-boiling silicone oils, low-boiling isoparaffin hydrocarbons, triglyceride, and ester oils are preferred. Exemplary of the low-boiling silicone oils are octamethylcyclotetrasiloxane, decamethylcyclopentasiloxane, and tetradecamethylcyclohexasiloxane. Exemplary of the ester oils are fatty acid esters of 6 to 20 carbon atoms and glycerol fatty acid esters.

In the cosmetic composition, the amount of oil varies with the form of cosmetic composition and may be determined appropriate as long as the effects of the invention are not impaired. Preferably the oil is contained in an amount of 0.1 to 95%, more preferably 1 to 80% by weight based on the total weight of the powder and the emulsion. Less than 0.1 wt % of the oil may fail to exert its slippery and humectant effects whereas more than 95 wt % of the oil tends to adversely affect storage stability.

Suitable solvents include medium to lower alcohols and aromatic alcohols. Lower alcohols of 1 to 4 carbon atoms such as isopropyl alcohol are preferred. In the cosmetic composition, the amount of solvent varies with the form of cosmetic composition and may be determined appropriate as long as the effects of the invention are not impaired. Preferably the solvent is contained in an amount of 0.1 to 80%, more preferably 1 to 50% by weight based on the total weight of the powder and the emulsion.

The material of the powder is not particularly limited as long as materials are acceptable for use in makeup cosmetic compositions. Typically the powder has an average particle size of 0.1 to 50 μm. For example, colorants such as inorganic coloring pigments, inorganic white pigments, and organic pigments, pearly agents, extender pigments, and organic powders are useful.

Suitable inorganic powder materials include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phiogopite, lepidolite, biotite, lithia mica, silicic acid, silicic anhydride, aluminum silicate, sodium silicate, sodium magnesium silicate, magnesium silicate, aluminum magnesium silicate, calcium silicate, barium silicate, strontium silicate, metal tungstates, hydroxyapatite, vermiculite, Higilite®, bentonite, montmorillonite, hectorite, zeolite, ceramic powder, calcium secondary phosphate, alumina, aluminum hydroxide, and boron nitride. Suitable organic powder materials include polyamide powder, polyester powder, polyethylene powder, polypropylene powder, polystyrene powder, polyurethane powder, benzoguanamine powder, polymethylbenzoguanamine powder, polytetrafluoroethylene powder, polymethyl methacrylate powder, cellulose, silk powder, nylon powder, 12-nylon, 6-nylon, silicone powder, polymethylsilsesquioxane spherical powder, styrene-acrylic acid copolymers, divinylbenzene-styrene copolymers, vinyl resins, urea resins, phenolic resins, fluoro-resins, silicon resins, acrylic resins, melamine resins, epoxy resins, polycarbonate resins, microcrystalline fibril powder, starch powder, and lauroyl lysine. Suitable surfactant metal salt powders include zinc stearate, aluminum stearate, calcium stearate, magnesium stearate, zinc myristate, magnesium myristate, zinc palmitate, zinc laurate, zinc cetylphosphate, calcium cetylphosphate, and zinc sodium cetylphosphate. Suitable color pigments include inorganic red pigments such as red iron oxide, iron oxide, iron hydroxide, iron titanate, inorganic brown pigments such as γ-iron oxide, inorganic yellow pigments such as yellow iron oxide and ochre, inorganic black pigments such as black iron oxide and carbon black, inorganic purple pigments such as manganese violet and cobalt violet, inorganic green pigments such as chromium hydroxide, chromium oxide, cobalt oxide, and cobalt titanate, inorganic blue pigments such as Prussian blue and ultramarine; lake-form tar pigments such as Red #3, Red #104, Red #106, Red #201, Red #202, Red #204, Red #205, Red #220, Red #226, Red #227, Red #228, Red #230, Red #401, Red #505, Yellow #4, Yellow #5, Yellow #202, Yellow #203, Yellow #204, Yellow #401, Blue #1, Blue #2, Blue #201, Blue #404, Green #3, Green #201, Green #204, Green #205, Orange #201, Orange #203, Orange #204, Orange #206, Orange #207, etc.; lake-form natural dyes such as carminic acid, laccaic acid, carthamin, brazilin and crocin. Suitable pearly pigments include titania-coated mica, titanated mica, iron oxide-treated titanated mica, bismuth oxychloride, titania-coated bismuth oxychloride, titania-coated talc, fish scales, and titania-coated colored mica. Suitable metal powder pigments include aluminum, gold, silver, copper, platinum and stainless steel in powder form. In a particular application, powder particles which have been surface treated with oils such as silicones may be used.

In the cosmetic composition, the amount of powder used varies with the form of cosmetic composition and may be determined appropriate as long as the effects of the invention are not impaired. Preferably the powder is contained in an amount of 0.1 to 95%, more preferably 0.1 to 50%, and even more preferably 0.5 to 40% by weight based on the total weight of the cosmetic composition. In the case of an aqueous cosmetic composition, water is contained in an amount of 5 to 80%, preferably 10 to 50% by weight based on the total weight of the cosmetic composition.

In formulating the foregoing ingredients, any suitable techniques may be used, for example, the technique of mixing the emulsion with other ingredients on a mixer until uniform.

Besides the foregoing ingredients, any other ingredients may be formulated in the cosmetic composition of the invention as long as the amount and nature of the ingredient are limited so as not to compromise the effects of the crosslinkable silicone rubber emulsion of the invention. Suitable other ingredients include surfactants, oily ingredients, polymers, gelling agents, alkaline agents, polyhydric alcohols, pH modifiers, UV absorbers, antioxidants, preservatives, anti-inflammatory agents, skin conditioning agents, perfumes and others commonly used in cosmetics. These other ingredients may be contained in an amount of 0 to 10% by weight of the cosmetic composition.

Examples of the cosmetic composition include makeup cosmetics such as foundations, face powders, eye shadow, eyeliner, eyebrow colors, cheek colors, lip colors, nail colors; basic cosmetics or skin care products such as milky lotion, cream, lotion, calamine lotion, sunscreen, suntan lotion, after shave lotion, pre-shave lotion, pack, acne treatment, and essence; hair care cosmetics such as shampoo, rinse, conditioner, hair color, hair tonic, setting agent, hair nutrient, permanent wave agent; body powder, deodorant, depilatory, soap, body shampoo, bath preparation, hand soap, and perfume. The cosmetic composition comprising the emulsion is best suited as a skin care product, mascara, eyeliner, eyebrow color or foundation.

EXAMPLE

Preparation Examples, Examples, and Comparative Examples are given below by way of illustration and not by way of limitation. All parts and % are by weight.

Preparation Example 1

A polymerization vessel equipped with a stirrer, condenser, thermometer and nitrogen gas inlet was charged with 300 parts of deionized water, heated at 80° C. with stirring, and then purged with nitrogen. With stirring, an emulsified liquid obtained by dissolving 30 parts of trimethylsiloxysilicic acid powder [$(CH_3)_3SiO_{0.5}$ units/$SiO_2$ units=0.7 (molar ratio); weight average molecular weight 4,000; average particle size 10 μm] in 30 parts of methyl methacrylate, 30 parts of ethyl acrylate, 228 parts of n-butyl methacrylate, and 12 parts of methacrylic acid and emulsifying with 24 parts of NIKKOL LMT (sodium lauroylmethyltaurine by Nikko Chemicals Co., Ltd.) was constantly added over 4 to 5 hours along with 0.5 part of vitamin C, 0.001 part of ferrous sulfate, and 1.5 parts of aqueous hydrogen peroxide (concentration ~30%), while the internal temperature was kept at 80° C. Reaction was continued at 80° C. for a further 1 hour to complete polymerization. The resulting emulsion was adjusted to nearly neutral with 5% ammonia water. The emulsion had a solid concentration of 40.1% and pH 6.9.

Preparation Example 2

A polymerization vessel equipped with a stirrer, condenser, thermometer and nitrogen gas inlet was charged with 300 parts of deionized water, heated at 80° C. with stirring, and then purged with nitrogen. With stirring, an emulsified liquid obtained by dissolving 30 parts of trimethylsiloxysilicic acid powder [$(CH_3)_3SiO_{0.5}$ units/$SiO_2$ units=0.7 (molar ratio); weight average molecular weight 4,000; average particle size 10 μm] in 30 parts of methyl methacrylate, 30 parts of ethyl acrylate, 228 parts of n-butyl methacrylate, and 12 parts of methacrylic acid and emulsifying with 30 parts of JT-05 (polyvinyl alcohol with a degree of saponification of 94 mol % and an average degree of polymerization of 500, by Japan Vam & Poval Co., Ltd.), was constantly added over 4 to 5 hours along with 0.5 part of vitamin C, 0.001 part of ferrous sulfate, and 1.5 parts of aqueous hydrogen peroxide (concentration ~30%), while the internal temperature was kept at 80° C. Reaction was continued at 80° C. for a further 1 hour to complete polymerization. The resulting emulsion had a solid concentration of 40.2% and pH 6.5.

Preparation Example 3

A polymerization vessel equipped with a stirrer, condenser, thermometer and nitrogen gas inlet was charged with 300 parts of deionized water, heated at 80° C. with stirring, and then purged with nitrogen. With stirring, an emulsified liquid obtained by dissolving 60 parts of trimethylsiloxysilicic acid decamethylcyclopentasiloxane solution [50 wt % trimethylsiloxysilicic acid; $(CH_3)_3SiO_{0.5}$ units/$SiO_2$ units=1.3 (molar ratio); weight average molecular weight 8,000] in 30 parts of methyl methacrylate, 30 parts of ethyl acrylate, 228 parts of n-butyl methacrylate, and 12 parts of methacrylic acid and emulsifying with 24 parts of NIKKOL LMT (sodium lauroylmethyltaurine by Nikko Chemicals Co., Ltd.) was constantly added over 4 to 5 hours along with 0.5 part of vitamin C, 0.001 part of ferrous sulfate, and 1.5 parts of aqueous hydrogen peroxide (concentration ~30%), while the internal temperature was kept at 80° C. Reaction was continued at 80° C. for a further 1 hour to complete polymerization. The resulting emulsion had a solid concentration of 39.8% and pH 6.4.

Preparation Example 4

A polymerization vessel equipped with a stirrer, condenser, thermometer and nitrogen gas inlet was charged with 300 parts of deionized water, heated at 80° C. with stirring, and then purged with nitrogen. With stirring, an emulsified liquid obtained by dissolving 9 parts of trimethylsiloxysilicic acid powder [$(CH_3)_3SiO_{0.5}$ units/$SiO_2$ units=0.7 (molar ratio); weight average molecular weight 4,000; average particle size 10 m] in 30 parts of methyl methacrylate, 30 parts of ethyl acrylate, 228 parts of n-butyl methacrylate, and 12 parts of methacrylic acid and emulsifying with 24 parts of NIKKOL LMT (sodium lauroylmethyltaurine by Nikko Chemicals Co., Ltd.) was constantly added over 4 to 5 hours along with 0.5 part of vitamin C, 0.001 part of ferrous sulfate, and 1.5 parts of aqueous hydrogen peroxide (concentration ~30%), while the internal temperature was kept at 80° C. Reaction was continued at 80° C. for a further 1 hour to complete polymerization. The resulting emulsion had a solid concentration of 39.5% and pH 6.7.

Preparation Example 5

A polymerization vessel equipped with a stirrer, condenser, thermometer and nitrogen gas inlet was charged with 300 parts of deionized water, heated at 80° C. with stirring, and then purged with nitrogen. With stirring, an emulsified liquid obtained by dissolving 135 parts of trimethylsiloxysilicic acid powder [$(CH_3)_3SiO_{0.5}$ units/$SiO_2$ units=0.7 (molar ratio); weight average molecular weight 4,000; average particle size 10 μm] in 30 parts of methyl methacrylate, 30 parts of ethyl acrylate, 228 parts of n-butyl methacrylate, and 12 parts of methacrylic acid and emulsifying with 24 parts of NIKKOL LMT (sodium lauroylmethyltaurine by Nikko Chemicals Co., Ltd.) was constantly added over 4 to 5 hours along with 0.5 part of vitamin C, 0.001 part of ferrous sulfate, and 1.5 parts of aqueous hydrogen peroxide (concentration ~30%), while the internal temperature was kept at 80° C. Reaction was continued at 80° C. for a further 1 hour to complete polymerization. The resulting emulsion had a solid concentration of 39.5% and pH 6.7.

Preparation Example 6

A polymerization vessel equipped with a stirrer, condenser, thermometer and nitrogen gas inlet was charged with 300 parts of deionized water, heated at 80° C. with stirring, and then purged with nitrogen. With stirring, an emulsified liquid obtained by dissolving 30 parts of trimethylsiloxysilicic acid powder [$(CH_3)_3SiO_{0.5}$ units/$SiO_2$ units=0.7 (molar ratio); weight average molecular weight 4,000; average particle size 10 μm] in 30 parts of methyl methacrylate, 100 parts of n-butyl acrylate, 158 parts of n-butyl methacrylate, and 12 parts of methacrylic acid and emulsifying with 24 parts of NIKKOL LMT (sodium lauroylmethyltaurine by Nikko Chemicals Co., Ltd.) was constantly added over 4 to 5 hours along with 0.5 part of vitamin C, 0.001 part of ferrous sulfate, and 1.5 parts of aqueous hydrogen peroxide (concentration ~30%), while the internal temperature was kept at 80° C. Reaction was continued at 80° C. for a further 1 hour to complete polymerization. The resulting emulsion was adjusted to nearly neutral with 5% ammonia water. The emulsion had a solid concentration of 40.4% and pH 6.8.

Comparative Preparation Example 1

A polymerization vessel equipped with a stirrer, condenser, thermometer and nitrogen gas inlet was charged with 300 parts of deionized water, heated at 80° C. with stirring, and then purged with nitrogen. With stirring, an emulsified liquid obtained by emulsifying 30 parts of methyl methacrylate, 30 parts of ethyl acrylate, 228 parts of n-butyl methacrylate, and 12 parts of methacrylic acid with 24 parts of NIKKOL LMT was constantly added over 4 to 5 hours along with 0.5 part of vitamin C, 0.001 part of ferrous sulfate, and 1.5 parts of aqueous hydrogen peroxide (concentration ~30%), while the internal temperature was kept at 80° C. Reaction was continued at 80° C. for a further 1 hour to complete polymerization. The resulting emulsion was adjusted to nearly neutral with 5% ammonia water. The emulsion had a solid concentration of 39.9% and pH 6.8.

Comparative Preparation Example 2

A polymerization vessel equipped with a stirrer, condenser, thermometer and nitrogen gas inlet was charged with 300 parts of deionized water, heated at 80° C. with stirring, and then purged with nitrogen. With stirring, an emulsified liquid obtained by dissolving 350 parts of trimethylsiloxysilicic acid powder [$(CH_3)_3SiO_{0.5}$ units/$SiO_2$ units=0.7 (molar ratio); weight average molecular weight 4,000; average particle size 10 μm] in 30 parts of methyl methacrylate, 30 parts of ethyl acrylate, 228 parts of n-butyl methacrylate, and 12 parts of methacrylic acid and emulsifying with 24 parts of NIKKOL LMT was constantly added over 4 to 5 hours along with 0.5 part of vitamin C, 0.001 part of ferrous sulfate, and 1.5 parts of aqueous hydrogen peroxide (concentration ~30%), while the internal temperature was kept at 80° C. Reaction was continued at 80° C. for a further 1 hour to complete polymerization. The resulting emulsion had a solid concentration of 41.0% and pH 6.4.

Properties of the emulsions obtained above were examined by the following tests, with the results shown in Table 1.

Measurement of Evaporation Residue (Solid Concentration)

A sample of about 1 g was weighed in an aluminum foil dish, placed in a dryer at 105-110° C., heated for 1 hour, taken out of the dryer, and allowed to cool in a desiccator. The weight of the sample after drying was measured, from which an evaporation residue was calculated according to the following equation.

$$R = (T-L)/(W-L) \times 100\%$$

R: evaporation residue (%)
W: weight (g) of aluminum foil dish containing sample prior to drying
L: weight (g) of aluminum foil dish
T: weight (g) of aluminum foil dish containing dried sample
Aluminum foil dish size: diameter 70 mm×height 12 mm Viscosity A liquid sample was kept at 23±0.5° C. and measured for viscosity by a Brookfield viscometer under conditions: No. 1 rotor and 6 rpm.

Average Particle Size

A sample of 0.01 g was weighed, dispersed in a solvent, and measured for average particle size (i.e., particle diameter corresponding to 50% in cumulative particle size distribution) by a laser diffraction type particle size distribution analyzer (LA-950V2 by Horiba Co., Ltd.) under conditions: circulation flow rate 2 and stirring rate 2.
Measurement temperature: 25±1° C.
Solvent: deionized water Storage Stability After an emulsion sample was stored at 40° C. for 2 months, its appearance was observed and any changes of viscosity and particle size were inspected. After 2 months of storage, all the emulsions of Preparation Examples showed neither appearance changes like separation nor changes of viscosity and particle size, indicating satisfactory stability with time.

Next, cosmetic compositions were prepared from the emulsions of the invention and evaluated for cosmetic performance.

Eyeliner

An oil-in-water type eyeliner cosmetic composition was prepared according to the formulation of Table 2.

Preparation Procedure

Example 1

The emulsion of Preparation Example 1 was combined with low-boiling cyclic silicone oil, polyether-modified silicone oil, black iron oxide, and mica. The contents were heated, dissolved and mixed. A preservative and purified water were added to the mixture, which was dispersed until uniform.

Examples 2 to 7 and Comparative Examples 1 to 3

Compositions were similarly prepared.

The compositions of Examples 1 to 7 and Comparative Examples 1 to 3 were evaluated as follows. The results are shown in Table 2.

(1) Lasting Quality

A panel of 10 members conducted an application test to evaluate the lasting quality of cosmetic. The evaluation criterion is as follows.

| Rating | Remarks |
|---|---|
| ⊚ | evaluated good by 8 or more of 10 members |
| ○ | evaluated good by 6 or more of 10 members |
| Δ | evaluated good by 4 or more of 10 members |
| X | evaluated good by 3 or less of 10 members |

(2) Water Resistance

A cosmetic composition was uniformly coated onto a nylon plate of 5 cm long×1 cm wide×1 cm thick and dried. The sample was set in a 20-ml glass vial containing 10 ml of

TABLE 1

| | | Preparation Example | | | | | | Comparative Preparation Example | |
|---|---|---|---|---|---|---|---|---|---|
| Components (pbw) | | 1 | 2 | 3 | 4 | 5 | 6 | 1 | 2 |
| Emulsion viscosity (mPa · s) | | 50 | 100 | 40 | 50 | 50 | 40 | 50 | 50 |
| | Particle size (nm) | 320 | 500 | 280 | 300 | 310 | 310 | 250 | 350 |
| After 40° C./ | Particle size (nm) | 310 | 510 | 270 | 290 | 300 | 300 | 250 | 340 |
| 2 months storage | Appearance | No change | No change | No change | No change | No change | No change | No change | Precipitate |

Note:
The value in parentheses represents an amount of 60% dispersion.

deionized water. Using a shaker, the vial was shaken for 10 minutes. The sample was examined whether or not the coating peeled off.

(3) Oil Resistance

A sample was prepared as in (2) and set in a 20-ml glass vial containing 10 ml of oil (triglyceride). The vial was shaken as in (2). The sample was examined whether or not the coating peeled off, and contacted with the finger to examine scraping strength and color transfer to finger.

(4) Adhesion

A sample was prepared as in (2) and set in a 20-ml glass vial containing 10 g of rice grain size Duracon resin (Polyplastics Co., Ltd.). The vial was shaken as in (2). The sample was examined for adhesion, i.e., whether or not the coating peeled off.

With respect to (2) to (4), the evaluation criterion is as follows.

| Rating | Remarks |
|---|---|
| ⊚ | very good |
| ○ | good |
| Δ | poor |
| X | extremely poor |

Mascara

A mascara cosmetic composition was prepared according to the formulation of Table 3.

Preparation Procedure

Example 8

The emulsion of Preparation Example 1 was combined with low-boiling cyclic silicone oil and polyether-modified silicone oil. The contents were heat dissolved. Black iron oxide and mica were added to the mixture, which was dispersed until uniform.

Examples 9 to 14 and Comparative Examples 4 to 6

Compositions were similarly prepared.

Like the eyeliner, the compositions of Examples 8 to 14 and Comparative Examples 4 to 6 were evaluated for (1) lasting quality, (2) water resistance, (3) oil resistance, and (4) adhesion. The results are shown in Table 3.

TABLE 2

| | Ingredients (pbw) | Example | | | | | | | Comparative Example | | |
|---|---|---|---|---|---|---|---|---|---|---|---|
| | | 1 | 2 | 3 | 4 | 5 | 6 | 7 | 1 | 2 | 3 |
| Formulation | Preparation Example 1 | 15 (6.0) | | | | | | 5 (2.0) | | | |
| | Preparation Example 2 | | 15 (6.0) | | | | | | | | |
| | Preparation Example 3 | | | 15 (6.0) | | | | | | | |
| | Preparation Example 4 | | | | 15 (5.9) | | | | | | |
| | Preparation Example 5 | | | | | 15 (5.9) | | | | | |
| | Preparation Example 6 | | | | | | 15 (6.1) | | | | |
| | Comparative Preparation Example 1 | | | | | | | | 15 (6.0) | | 14 (5.6) |
| | Comparative Preparation Example 2 | | | | | | | | | 15 (6.2) | |
| | Trimethylsiloxysilicic acid | | | | | | | | | | 1 |
| | Low-boiling cyclic silicone oil | 30 | 30 | 30 | 30 | 30 | 30 | 30 | 30 | 30 | 30 |
| | Polyether-modified silicone oil | 4 | 4 | 4 | 4 | 4 | 4 | 4 | 4 | 4 | 4 |
| | Black iron oxide | 10 | 10 | 10 | 10 | 10 | 10 | 10 | 10 | 10 | 10 |
| | Mica | 5 | 5 | 5 | 5 | 5 | 5 | 5 | 5 | 5 | 5 |
| | Preservative | 0.5 | 0.5 | 0.5 | 0.5 | 0.5 | 0.5 | 0.5 | 0.5 | 0.5 | 0.5 |
| | Purified water | 35.5 | 35.5 | 35.5 | 35.5 | 35.5 | 35.5 | 45.5 | 35.5 | 35.5 | 35.5 |
| Evaluation | Lasting quality | ⊚ | ⊚ | ⊚ | ⊚ | ⊚ | ⊚ | ⊚ | X | ○ | ○ |
| | Water resistance | ⊚ | ⊚ | ⊚ | ⊚ | ⊚ | ⊚ | ⊚ | Δ | Δ | Δ |
| | Oil resistance | ⊚ | ⊚ | ○ | ⊚ | ⊚ | ⊚ | ⊚ | Δ | X | Δ |
| | Adhesion | ⊚ | ⊚ | ⊚ | ⊚ | ⊚ | ⊚ | ⊚ | ○ | ○ | ○ |

Trimethylsiloxysilicic acid: $(CH_3)_3SiO_{0.5}$ units/$SiO_2$ units = 0.7 (molar ratio); weight average molecular weight 4,000; average particle size 10 μm.
Note:
The value in parentheses represents an amount of solids.

TABLE 3

| Ingredients (pbw) | | Example 8 | Example 9 | Example 10 | Example 11 | Example 12 | Example 13 | Example 14 | Comparative Example 4 | Comparative Example 5 | Comparative Example 6 |
|---|---|---|---|---|---|---|---|---|---|---|---|
| Formulation | Preparation Example 1 | 60 (24.1) | | | | | | 20 (8.0) | | | |
| | Preparation Example 2 | | 60 (24.1) | | | | | | | | |
| | Preparation Example 3 | | | 60 (23.9) | | | | | | | |
| | Preparation Example 4 | | | | 60 (23.7) | | | | | | |
| | Preparation Example 5 | | | | | 60 (23.7) | | | | | |
| | Preparation Example 6 | | | | | | 60 (24.2) | | | | |
| | Comparative Preparation Example 1 | | | | | | | | 60 (23.9) | | 50 (22.7) |
| | Comparative Preparation Example 2 | | | | | | | | | 60 (24.6) | |
| | Trimethylsiloxysilicic acid | | | | | | | | | | 3 |
| | Low-boiling cyclic silicone oil | 21 | 21 | 21 | 21 | 21 | 21 | 61 | 21 | 21 | 21 |
| | Polyether-modified silicone oil | 2 | 2 | 2 | 2 | 2 | 2 | 2 | 2 | 2 | 2 |
| | Black iron oxide | 7 | 7 | 7 | 7 | 7 | 7 | 7 | 7 | 7 | 7 |
| | Mica | 10 | 10 | 10 | 10 | 10 | 10 | 10 | 10 | 10 | 10 |
| Evaluation | Lasting quality | ⊚ | ⊚ | ⊚ | ⊚ | ⊚ | ⊚ | ○ | Δ | Δ | ○ |
| | Water resistance | ⊚ | ⊚ | ⊚ | ⊚ | ⊚ | ⊚ | ⊚ | Δ | Δ | Δ |
| | Oil resistance | ⊚ | ⊚ | ⊚ | ⊚ | ⊚ | ⊚ | ⊚ | X | Δ | Δ |
| | Adhesion | ⊚ | ⊚ | ⊚ | ⊚ | ⊚ | ⊚ | ⊚ | ○ | Δ | ○ |

Trimethylsiloxysilicic acid: $(CH_3)_3SiO_{0.5}$ units/$SiO_2$ units = 0.7 (molar ratio); weight average molecular weight 4,000; average particle size 10 μm.
Note:
The value in parentheses represents an amount of solids.

Liquid Foundation

A liquid foundation cosmetic composition was prepared according to the formulation of Table 4.

Preparation Procedure

Example 15

The emulsion of Preparation Example 1, KF-6028, organic-modified bentonite, trioctanoin, a portion of KF-96A-6cs and a portion of KF-995 were uniformly dispersed. This dispersion was mixed with a solution of dipropylene glycol and sodium citrate in purified water. This was further mixed with the remaining portions of KF-96A-6cs and KF-995 and a dispersion of pigment in KP-578.

Examples 16 to 21 and Comparative Examples 7 to 9

Compositions were similarly prepared.

Like the eyeliner, the compositions of Examples 15 to 21 and Comparative Examples 7 to 9 were evaluated for (1) lasting quality, (2) water resistance, (3) oil resistance, and (4) adhesion. The results are shown in Table 4.

TABLE 4

| Ingredients (pbw) | | Example 15 | Example 16 | Example 17 | Example 18 | Example 19 | Example 20 | Example 21 | Comparative Example 7 | Comparative Example 8 | Comparative Example 9 |
|---|---|---|---|---|---|---|---|---|---|---|---|
| Formulation | Preparation Example 1 | 8.5 (3.4) | | | | | | | 15 (6.1) | | |
| | Preparation Example 2 | | 8.5 (3.4) | | | | | | | | |
| | Preparation Example 3 | | | 8.5 (3.4) | | | | | | | |
| | Preparation Example 4 | | | | 8.5 (3.4) | | | | | | |
| | Preparation Example 5 | | | | | 8.5 (3.4) | | | | | |
| | Preparation Example 6 | | | | | | 8.5 (3.4) | | | | |
| | Comparative Preparation Example 1 | | | | | | | | 8.5 (3.4) | | 7.5 (3.0) |
| | Comparative Preparation Example 2 | | | | | | | | | 8.5 (3.5) | |
| | Trimethylsiloxysilicic acid | | | | | | | | | | 1 |

TABLE 4-continued

|  | Ingredients (pbw) | Example 15 | 16 | 17 | 18 | 19 | 20 | 21 | Comparative Example 7 | 8 | 9 |
|---|---|---|---|---|---|---|---|---|---|---|---|
|  | KF-6028 | 2 | 2 | 2 | 2 | 2 | 2 | 2 | 2 | 2 | 2 |
|  | Organic-modified bentonite | 1.2 | 1.2 | 1.2 | 1.2 | 1.2 | 1.2 | 1.2 | 1.2 | 1.2 | 1.2 |
|  | Trioctanoin | 5 | 5 | 5 | 5 | 5 | 5 | 5 | 5 | 5 | 5 |
|  | KF-96A-6cs | 6.5 | 6.5 | 6.5 | 6.5 | 6.5 | 6.5 | 6.5 | 6.5 | 6.5 | 6.5 |
|  | KF-995 | 22.6 | 22.6 | 22.6 | 22.6 | 22.6 | 22.6 | 22.6 | 22.6 | 22.6 | 22.6 |
|  | KP-578 | 0.5 | 0.5 | 0.5 | 0.5 | 0.5 | 0.5 | 0.5 | 0.5 | 0.5 | 0.5 |
|  | Pigment | 10 | 10 | 10 | 10 | 10 | 10 | 10 | 10 | 10 | 10 |
|  | Dipropylene glycol | 5 | 5 | 5 | 5 | 5 | 5 | 5 | 5 | 5 | 5 |
|  | Sodium citrate | 0.2 | 0.2 | 0.2 | 0.2 | 0.2 | 0.2 | 0.2 | 0.2 | 0.2 | 0.2 |
|  | Purified water | 38.5 | 38.5 | 38.5 | 38.5 | 38.5 | 38.5 | 32 | 38.5 | 38.5 | 38.5 |
| Evaluation | Lasting quality | ◎ | ◎ | ◎ | ◎ | ◎ | ◎ | ◎ | ○ | Δ | ○ |
|  | Water resistance | ◎ | ◎ | ◎ | ◎ | ◎ | ◎ | ◎ | Δ | Δ | Δ |
|  | Oil resistance | ◎ | ○ | ○ | ◎ | ○ | ◎ | ○ | X | X | Δ |
|  | Adhesion | ◎ | ◎ | ◎ | ◎ | ◎ | ◎ | ◎ | Δ | ○ | ○ |

Trimethylsiloxysilicic acid: $(CH_3)_3SiO_{0.5}$ units/$SiO_2$ units = 0.7 (molar ratio); weight average molecular weight 4,000; average particle size 10 μm.
Note:
The value in parentheses represents an amount of solids.
KF-6028: polyether-modified silicone oil by Shin-Etsu Chemical Co., Ltd.
KF-96A-6cs: dimethylsilicone oil (viscosity 6 mPa · s) by Shin-Etsu Chemical Co., Ltd.
KF-995: decamethylpentacyclosiloxane by Shin-Etsu Chemical Co., Ltd.
KP-578: acrylate/ethylhexyl acrylate/dimethicone methacrylate copolymer by Shin-Etsu Chemical Co., Ltd.

Sunscreen Lotion

A sunscreen lotion cosmetic composition was prepared according to the formulation of Table 5.

Preparation Procedure

Example 22

The emulsion of Preparation Example 1, KF-96A-6cs, KF-995, KF-6028, and tridecyl isononanoate were uniformly mixed. This mixture was mixed with a uniform mixture of dipropylene glycol, sodium citrate and sodium chloride in purified water. To this mixture, SPD-T5 and SPD-Z5 were added and the contents were uniformly mixed.

Examples 23 to 28 and Comparative Examples 10 to 12

Compositions were similarly prepared.

Like the eyeliner, the compositions of Examples 22 to 28 and Comparative Examples 10 to 12 were evaluated for (1) lasting quality, (2) water resistance, (3) oil resistance, and (4) adhesion. The results are shown in Table 5.

TABLE 5

|  |  | Example 22 | 23 | 24 | 25 | 26 | 27 | 28 | Comparative Example 10 | 11 | 12 |
|---|---|---|---|---|---|---|---|---|---|---|---|
| Formulation | Preparation Example 1 | 5 (2.0) |  |  |  |  |  |  | 10 (4.0) |  |  |
|  | Preparation Example 2 |  | 5 (2.0) |  |  |  |  |  |  |  |  |
|  | Preparation Example 3 |  |  | 5 (2.0) |  |  |  |  |  |  |  |
|  | Preparation Example 4 |  |  |  | 5 (2.0) |  |  |  |  |  |  |
|  | Preparation Example 5 |  |  |  |  | 5 (2.0) |  |  |  |  |  |
|  | Preparation Example 6 |  |  |  |  |  | 5 (2.0) |  |  |  |  |
|  | Comparative Preparation Example 1 |  |  |  |  |  |  |  | 5 (2.0) |  | 4 (1.6) |
|  | Comparative Preparation Example 2 |  |  |  |  |  |  |  |  | 5 (2.1) |  |
|  | Trimethylsiloxysilicic acid |  |  |  |  |  |  |  |  |  | 1 |
|  | KF-96A-6cs | 5 | 5 | 5 | 5 | 5 | 5 | 5 | 5 | 5 | 5 |
|  | KF-995 | 5 | 5 | 5 | 5 | 5 | 5 | 5 | 5 | 5 | 5 |
|  | KF-6028 | 1 | 1 | 1 | 1 | 1 | 1 | 1 | 1 | 1 | 1 |
|  | Tridecyl isononanoate | 4 | 4 | 4 | 4 | 4 | 4 | 4 | 4 | 4 | 4 |
|  | SPD-T5 | 25 | 25 | 25 | 25 | 25 | 25 | 25 | 25 | 25 | 25 |
|  | SPD-Z5 | 35 | 35 | 35 | 35 | 35 | 35 | 35 | 35 | 35 | 35 |
|  | Dipropylene glycol | 2 | 2 | 2 | 2 | 2 | 2 | 2 | 2 | 2 | 2 |
|  | Sodium citrate | 0.2 | 0.2 | 0.2 | 0.2 | 0.2 | 0.2 | 0.2 | 0.2 | 0.2 | 0.2 |

TABLE 5-continued

| | Ingredients (pbw) | Example | | | | | | | Comparative Example | | |
|---|---|---|---|---|---|---|---|---|---|---|---|
| | | 22 | 23 | 24 | 25 | 26 | 27 | 28 | 10 | 11 | 12 |
| | Sodium chloride | 1 | 1 | 1 | 1 | 1 | 1 | 1 | 1 | 1 | 1 |
| | Purified water | 16.8 | 16.8 | 16.8 | 16.8 | 16.8 | 16.8 | 11.8 | 16.8 | 16.8 | 16.8 |
| Evaluation | Lasting quality | ◉ | ◉ | ○ | ◉ | ◉ | ◉ | ○ | Δ | Δ | ○ |
| | Water resistance | ◉ | ◉ | ◉ | ◉ | ◉ | ◉ | ◉ | Δ | Δ | Δ |
| | Oil resistance | ◉ | ○ | ○ | ◉ | ○ | ◉ | ○ | X | X | Δ |
| | Adhesion | ◉ | ◉ | ◉ | ◉ | ◉ | ◉ | ◉ | Δ | ○ | ○ |

Trimethylsiloxysilicic acid: $(CH_3)_3SiO_{0.5}$ units/$SiO_2$ units = 0.7 (molar ratio); weight average molecular weight 4,000; average particle size 10 μm.

Note:
The value in parentheses represents an amount of solids.
KF-96A-6cs: dimethylsilicone oil (viscosity 6 mPa·s) by Shin-Etsu Chemical Co., Ltd.
KF-995: decamethylpentacyclosiloxane by Shin-Etsu Chemical Co., Ltd.
KF-6028: polyether-modified silicone oil by Shin-Etsu Chemical Co., Ltd.
SPD-T5: titania dispersion of cosmetic grade by Shin-Etsu Chemical Co., Ltd.
SPD-Z5: zinc oxide dispersion of cosmetic grade by Shin-Etsu Chemical Co., Ltd.

Japanese Patent Application No. 2013-174421 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An emulsion obtained from emulsion polymerization of a mixture of (a) 1 to 50% by weight of a triorganosiloxysilicic acid and (b) 50 to 99% by weight of an ethylenically unsaturated group-containing monomer, the total of components (a) and (b) being 100% by weight, in the presence of (c) at least one emulsion stabilizer selected from the group consisting of an anionic surfactant, nonionic surfactant, and polyvinyl alcohol.

2. The emulsion of claim 1 wherein the triorganosiloxysilicic acid (a) comprises $SiO_2$ units and $R_3SiO_{0.5}$ units (wherein R is an alkyl group of 1 to 6 carbon atoms) in a molar ratio of 0.5 to 2.0, and the total amount of $SiO_2$ units and $R_3SiO_{0.5}$ units accounts for at least 90 mol % of the triorganosiloxysilicic acid (a).

3. The emulsion of claim 2 wherein the triorganosiloxysilicic acid (a) is trimethylsiloxysilicic acid in which R is methyl in $R_3SiO_{0.5}$ units.

4. The emulsion of claim 1 wherein the ethylenically unsaturated group-containing monomer (b) is selected from the group consisting of ethylene, propylene, chlorine-containing ethylenically unsaturated monomers, aromatic vinyl monomers, vinyl carboxylate monomers, conjugated diene monomers, ethylenically unsaturated monocarboxylic acid esters, ethylenically unsaturated dicarboxylic acid esters, ethylenically unsaturated monocarboxylic acids, ethylenically unsaturated dicarboxylic acids, alcoholic hydroxyl-containing ethylenically unsaturated monomers, epoxy-containing ethylenically unsaturated monomers, alkoxy-containing ethylenically unsaturated monomers, nitrile-containing ethylenically unsaturated monomers, amide-containing ethylenically unsaturated monomers, amino-containing ethylenically unsaturated monomers, monomers having at least two ethylenically unsaturated groups, and mixtures thereof.

5. The emulsion of claim 1 wherein the ethylenically unsaturated group-containing monomer (b) is selected from the group consisting of acrylic acid, methacrylic acid, alkyl acrylates, alkyl methacrylates, and mixtures thereof.

6. The emulsion of claim 1 wherein the stabilizer (c) is selected from the group consisting of acylamino acid salts, acyltaurine salts, aliphatic soaps, alkyl phosphates, and mixtures thereof.

7. A cosmetic composition, comprising:
the emulsion of claim 1; and
at least one additional ingredient selected from the group consisting of oil, solvent, and powder.

8. A method of treating skin, hair, or nails comprising applying the cosmetic composition of claim 7 to skin, hair, or nails.

9. A makeup cosmetic composition comprising 0.1 to 30% by weight calculated as solids and based on the composition of the emulsion of claim 1, which composition is a skin care product, mascara, eyeliner, eyebrow color or foundation.

10. A method for preparing an emulsion comprising the steps of
dissolving (a) 1 to 50% by weight of a triorganosiloxysilicic acid in (b) 50 to 99% by weight of at least one ethylenically unsaturated group-containing monomer to form a mixture, the total of components (a) and (b) being 100% by weight,
adding 0.1 to 20 parts by weight of (c) at least one emulsion stabilizer selected from the group consisting of an anionic surfactant, nonionic surfactant, and polyvinyl alcohol to 100 parts by weight of the mixture, and
effecting emulsion polymerization.

* * * * *